(12) United States Patent
Haddach

(10) Patent No.: US 6,583,143 B2
(45) Date of Patent: Jun. 24, 2003

(54) CRF RECEPTOR ANTAGONISTS AND METHODS RELATING THERETO

(75) Inventor: Mustapha Haddach, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 82 days.

(21) Appl. No.: 10/036,752

(22) Filed: Dec. 21, 2001

(65) Prior Publication Data

US 2002/0128265 A1 Sep. 12, 2002

Related U.S. Application Data

(60) Provisional application No. 60/258,685, filed on Dec. 28, 2000.

(51) Int. Cl.[7] .................... C07D 471/18; C07D 487/18; A61K 31/53; A61P 9/10; A61P 25/22
(52) U.S. Cl. ........................................ 514/243; 544/184
(58) Field of Search ................... 544/184; 514/243

(56) References Cited

U.S. PATENT DOCUMENTS 5,670,503 A * 9/1997 Kawai et al. ............... 514/243

FOREIGN PATENT DOCUMENTS

| WO | WO 00/27846 | 5/2000 |
|----|-------------|--------|
| WO | WO 00/27850 | 5/2000 |

OTHER PUBLICATIONS

Mitchell, Neurosci. Biobehav. Rev. 22(5); 635–651, 1998.*

* cited by examiner

*Primary Examiner*—Venkataraman Balasubramanian
(74) *Attorney, Agent, or Firm*—Seed IP Law Group PLLC

(57) ABSTRACT

CRF receptor antagonists are disclosed which have utility in the treatment of a variety of disorders, including the treatment of disorders manifesting hypersecretion of CRF in a warm-blooded animals, such as stroke. The CRF receptor antagonists of this invention have the following structure:

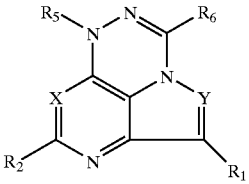

including stereoisomers, prodrugs and pharmaceutically acceptable salts thereof, wherein $R_1$, $R_2$, $R_5$, $R_6$, X and Y are as defined herein. Compositions containing a CRF receptor antagonist in combination with a pharmaceutically acceptable carrier are also disclosed, as well as methods for use of the same

18 Claims, No Drawings

CRF RECEPTOR ANTAGONISTS AND METHODS RELATING THERETO

This application claims benefit of U.S. Provisional application 60/258,685 filed on Dec. 28, 2000.

BACKGROUND OF THE INVENTION

1. Field of the Invention

This invention relates generally to CRF receptor antagonists, and to methods of treating disorders by administration of such antagonists to a warm-blooded animal in need thereof.

2. Description of the Related Art

The first corticotropin-releasing factor (CRF) was isolated from ovine hypothalmi and identified as a 41-amino acid peptide (Vale et al., *Science* 213:1394–1397, 1981). Subsequently, sequences of human and rat CRF were isolated and determined to be identical, but different from ovine CRF in 7 of the 41 amino acid residues (Rivier et al., *Proc. Natl. Acad. Sci. USA* 80:4851, 1983; Shibahara et al., *EMBO J.* 2:775, 1983).

CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., *Science* 213:1394–1397, 1981). Briefly, CRF is believed to initiate its biological effects by binding to a plasma membrane receptor which has been found to be distributed throughout the brain (DeSouza et al., *Science* 224:1449–1451, 1984), pituitary (DeSouza et al., *Methods Enzymol.* 124:560, 1986; Wynn et al., *Biochem. Biophys. Res. Comm.* 110:602–608, 1983), adrenals (Udelsman et al., *Nature* 319:147–150, 1986) and spleen (Webster, E. L., and E. B. DeSouza, *Endocrinology* 122:609–617, 1988). The CRF receptor is coupled to a GTP-binding protein (Perrin et al., *Endocrinology* 118:1171–1179, 1986) which mediates CRF-stimulated increase in intracellular production of cAMP (Bilezikjian, L. M., and W. W. Vale, *Endocrinology* 113:657–662, 1983). The receptor for CRF has now been cloned from rat (Perrin et al., *Endo* 133(6):3058–3061, 1993), and human brain (Chen et al., *PNAS* 90(19):8967–8971, 1993; Vita et al., *FEBS* 335(1):1–5, 1993). This receptor is a 415 amino acid protein comprising seven membrane spanning domains. A comparison of identity between rat and human sequences shows a high degree of homology (97%) at the amino acid level.

In addition to its role in stimulating the production of ACTH and POMC, CRF is also believed to coordinate many of the endocrine, autonomic, and behavioral responses to stress, and may be involved in the pathophysiology of affective disorders. Moreover, CRF is believed to be a key intermediary in communication between the immune, central nervous, endocrine and cardiovascular systems (Crofford et al., *J. Clin. Invest.* 90:2555–2564, 1992; Sapolsky et al., *Science* 238:522–524, 1987; Tilders et al., *Regul. Peptides* 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., *Nature* 297:331, 1982), persistent activation of the electroencephalogram (Ehlers et al., *Brain Res.* 278:332, 1983), stimulation of the sympathoadrenomedullary pathway (Brown et al., *Endocrinology* 110:928, 1982), an increase of heart rate and blood pressure (Fisher et al., *Endocrinology* 110:2222, 1982), an increase in oxygen consumption (Brown et al., *Life Sciences* 30:207, 1982), alteration of gastrointestinal activity (Williams et al., *Am. J. Physiol.* 253:G582, 1987), suppression of food consumption (Levine et al., *Neuropharmacology* 22:337, 1983), modification of sexual behavior (Sirinathsinghji et al., *Nature* 305:232, 1983), and immune function compromise (Irwin et al., *Am. J Physiol.* 255:R744, 1988). Furthermore, clinical data suggests that CRF may be hypersecreted in the brain in depression, anxiety-related disorders, and anorexia nervosa. (DeSouza, *Ann. Reports in Med. Chem.* 25:215–223, 1990). Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., *Science* 224:889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported. For example, substituted 4-thio-5-oxo-3-pyrazoline derivatives (Abreu et al., U.S. Pat. No. 5,063,245) and substituted 2-aminothiazole derivatives (Courtemanche et al., Australian Patent No. AU-A-41399/93) have been reported as CRF receptor antagonists. These particular derivatives were found to be effective in inhibiting the binding of CRF to its receptor in the 1–10 $\mu$M range and 0.1–10 $\mu$M range, respectively.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

BRIEF SUMMARY OF THE INVENTION

In brief, this invention is generally directed to CRF receptor antagonists, and more specifically to CRF receptor antagonists having the following general structure (I):

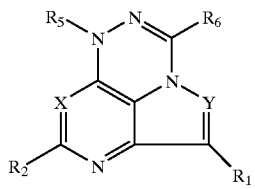

including stereoisomers, prodrugs and pharmaceutically acceptable salts thereof, wherein $R_1$, $R_2$, $R_5$, $R_6$, X and Y are as defined below.

The CRF receptor antagonists of this invention have utility over a wide range of therapeutic applications, and may be used to treat a variety of disorders or illnesses, including stress-related disorders. Such methods include administering an effective amount of a CRF receptor antagonist of this invention, preferably in the form of a pharmaceutical composition, to an animal in need thereof. Accordingly, in another embodiment, pharmaceutical compositions are disclosed containing one or more CRF receptor antagonists of this invention in combination with a pharmaceutically acceptable carrier and/or diluent.

These and other aspects of the invention will be apparent upon reference to the following detailed description. To this end, various references are set forth herein which describe in more detail certain procedures, compounds and/or compositions, and are hereby incorporated by reference in their entirety.

DETAILED DESCRIPTION OF THE INVENTION

The present invention is directed generally to compounds useful as corticotropin-releasing factor (CRF) receptor antagonists having the following structure (I):

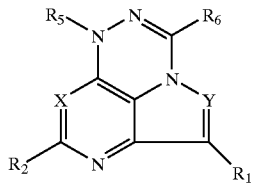

including stereoisomers, prodrugs and pharmaceutically acceptable salts thereof,
wherein:
X is nitrogen or $CR_3$;
Y is nitrogen or $CR_4$;
$R_1$ is alkyl, substituted alkyl, —$NR_7R_8$, aryl, substituted aryl, heteroaryl or substituted heteroaryl;
$R_2$ is hydrogen, alkyl, alkoxy, thioalkyl or haloalkyl;
$R_3$ is hydrogen, alkyl, halo or haloalkyl;
R4 is hydrogen, halogen, —$NR_7R_8$, alkyl, alkoxy, thioalkyl or haloalkyl;
$R_5$ is hydrogen, alkyl, substituted alkyl, aryl, substituted aryl, heteroaryl or substituted heteroaryl;
$R_6$ is hydrogen, alkyl, substituted alkyl, —$NR_7R_8$, —$OR_9$, —$SR_9$, aryl, substituted aryl, heteroaryl or substituted heteroaryl;
$R_7$ and $R_8$ are the same or different and independently hydrogen, alkyl, substituted alkyl, aryl, substituted aryl, heteroaryl or substituted heteroaryl; and $R_9$ is alkyl, substituted alkyl, aryl, substituted aryl, heteroaryl or substituted heteroaryl.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —$CH_2$cyclopropyl, —$CH_2$cyclobutyl, —$CH_2$cyclopentyl, —$CH_2$cyclohexyl, and the like; while unsaturated cyclic alkyls include cyclopentenyl and cyclohexenyl, and the like. Cyclic alkyls, also referred to as "homocyclic rings," and include di- and poly-homocyclic rings such as decalin and adamantyl. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl, —$CH_2$—(1 or 2-naphthyl), —$(CH_2)_2$phenyl, —$(CH_2)_3$phenyl, —CH(phenyl)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls include (but are not limited to) furyl, benzofuranyt, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, oxadiazolyl, thiadiazolyl, benzisoxazolyl, triazolyl, tetrazolyl, indazolyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH₂morpholinyl, and the like.

The term "substituted" as used herein means any of the above groups (e.g., alkyl, aryl, arylalkyl, heteroaryl, heteroarylalkyl, heterocycle and heterocyclealkyl) wherein at least one hydrogen atom is replaced with a substituent. In the case of an oxo substituent ("=O") two hydrogen atoms are replaced. When substituted, "substituents" within the context of this invention include halogen, hydroxy, oxo, cyano, nitro, amino, alkylamino, dialkylamino, alkyl, alkoxy, alkylthio, haloalkyl, aryl, substituted aryl, arylalkyl, substituted arylalkyl, heteroaryl, substituted beteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$R$_b$, —NR$_a$C(=O)OR$_b$, —NR$_a$SO$_2$R$_b$, —OR$_a$, —C(=O)R$_a$, —C(=O)OR$_a$, —C(=O)NR$_a$R$_b$, —OC(=O)NR$_a$R$_b$, —SR$_a$, —SOR$_a$, —OS(=O)$_2$R$_a$, —S(=O)$_2$OR$_a$, wherein R$_a$ and R$_b$ are the same or different and independently hydrogen, alkyl, substituted alkyl (such as haloalkyl), aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

"Thioalkyl" means an alkyl moiety attached through a sulfur bridge (i.e., —S-alkyl) such as methylthio, ethylthio, and the like.

"Alkylamino" and "dialkylamino" mean an amino substituted with one alkyl or with two alkyls, respectively, such as methylamino, ethylamino, dimethylamino, diethylamino, and the like.

"Hydroxyalkyl" means an alkyl substituted with at least one hydroxyl group.

"Alkylcarbonylalkyl" represents an alkyl substituted with a —C(=O)alkyl group.

"Alkylcarbonyloxyalkyl" represents an alkyl substituted with a —C(=O)Oalkyl group or a —OC(=O)alkyl group.

"Alkyloxyalkyl" represents an alkyl substituted with a —O-alkyl group.

"Alkylthioalkyl" represents an alkyl substituted with a —S-alkyl group.

Depending upon the Y and X substituents, representative compounds of this invention have one of the following structures (II), (III), (IV) or (V):

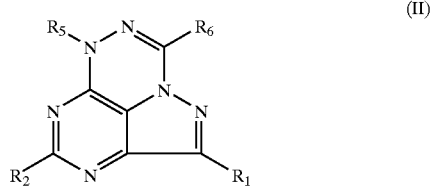
(II)

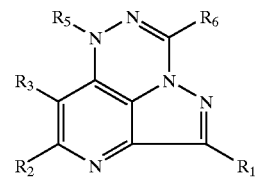
(III)

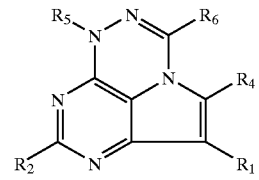
(IV)

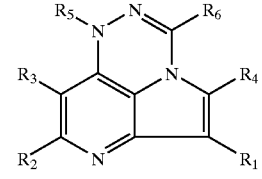
(V)

In more specific embodiments of this invention, representative R$_1$ groups of this invention include (but are not limited to) 2,4-dichlorophenyl, 2,4-dimethyl-phenyl, 2-chloro-4-methylphenyl, 2-methyl-4-chlorophenyl, 2,4,6-trimethylphenyl, 2-chloro-4-methoxyphenyl, 2-methyl-4-methoxyphenyl, 2,4-dimethoxyphenyl, 2-trifluoromethyl-4-chlorophenyl, 3-methoxy-4-chlorophenyl, 2,5-dimethoxy-4-chlorophenyl, 2-methoxy-4-trichloromethylphenyl, 2-methoxy-4-isopropylphenyl, 2-methoxy-4-trifluoromethylphenyl, 2-methoxy-4-isopropylphenyl 2-methoxy-4-methylphenyl, 4-methyl-6-dimethylaminopyridin-3-yl, 4-dimethylamino-6-methyl-pyridin-3-yl, 6-dimethylamino-pyridin-3-yl and 4-dimethylamino-pyridin-3-yl.

Similarly, representative R$_2$ groups include hydrogen and alkyl such as methyl and ethyl, while representative R$_3$ groups include hydrogen, halogen such as chlorine, fluorine and bromine, alkyl such as methyl and ethyl, and haloalkyl such as trifluoromethyl.

Representative R$_4$ groups include hydrogen, halogen such as chlorine, fluorine and bromine, alkyl such as methyl and ethyl, haloalkyl such as trifluoromethyl, substituted amino such as methyl or dimethylamino, thioalkyl such as thiomethyl and alkoxy such as ethoxy. Representative R$_5$ groups include hydrogen, alkyl such as methyl, ethyl, propyl, butyl, pentyl, heptyl, octyl, nonyl including branched and straight chains, saturated and unsaturated, substituted alkyl such as benzyl and phenethyl, aryl such as phenyl or naphthyl, and heterocycle such as pyridyl or furyl. Representative R$_6$ groups include hydrogen and alkyl such as methyl or ethyl. Representative R$_7$ and R$_8$ groups are as disclosed above for R$_5$.

The compounds of the present invention may generally be utilized as the free base. Alternatively, the compounds of this invention may be used in the form of acid addition salts. Acid addition salts of the free base amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

The compounds of structure (I) may be made according to the organic synthesis techniques known to those skilled in this field, as well as by the representative methods set forth in the Examples.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g., $[^{125}I]$ tyrosine-CRF) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)).

With reference to CRF receptor binding affinities, CRF receptor antagonists of this invention have a $K_i$ of less than 10 μM. In a preferred embodiment of this invention, a CRF receptor antagonist has a $K_i$ of less than 1 μM, more preferably less than 0.25 μM (i.e., 250 nM), and most preferably less than 100 nM. To this end, compounds 7–9, 7–10 and 8–3 (see Examples 7 and 8) have $K_i$ values of less than 100 nM. As set forth in greater detail below, the $K_i$ values of representative compounds of this invention were assayed by the methods set forth in Example 9. The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various disease states, as well as stroke. Other uses of the CRF antagonists of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder—that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in *Remington's Pharmaceutical Sciences*, Gennaro, Ed., Mack Publishing Co., Easton, Pa. 1990.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

In another embodiment, compounds of this invention may be used as Positron Emission Tomography (PET) ligands, Single Photon Emission Computed Tomography (SPECT) ligands, or other diagnostic radiopharmaceutical agents. Incorporation of an appropriate isotope (such as $^{11}C$ or $^{18}F$ for PET or $^{125}I$ in the case of SPECT) provides agents useful for the diagnosis or therapeutic management of a patient. In addition, use of a compound of the present invention may provide a physiological, functional, or biological assessment of a patient or provide disease or pathology detection and assessment.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, Cushing's disease, infantile spasms, epilepsy, and substance abuse or withdrawal.

The following examples are provided for purposes of illustration, not limitation.

EXAMPLES

The CRF receptor antagonists of this invention may be prepared by the methods disclosed in Examples 1 through 8. Example 9 presents a method for determining the receptor binding activity ($K_i$), while Example 10 discloses an assay for screening compounds of this invention for CRF-stimulated adenylate cyclase activity.

Example 1

Synthesis of Intermediate for Structure (II)

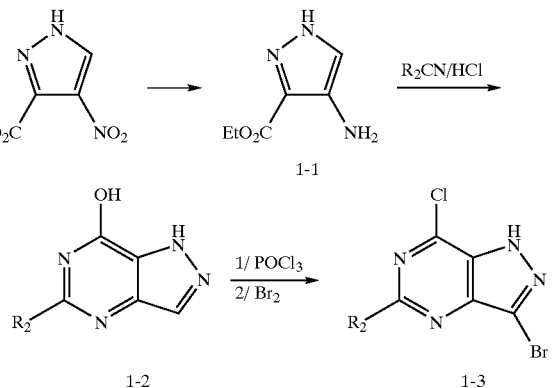

Compound 1-1

The 4-nitro pyrazole is added to a suspension of palladium on carbon 10% in ethanol (100 mL). The mixture is shaken for 3 hours under hydrogen gas (40 psi) at room temperature. Completion of the reaction is checked by TLC (ethylacetate/hexane 1/1, nitropyrazole Rf 0.6, UV active, amino-pyrazole Rf 0.1, UV active). The catalyst is removed by filtration through celite and the solvents are evaporated. The product 1-1, a burgundy solid, is used in the following step without purification Compound 1-2

A solution of 4-amino pyrazole 1-1 (0.4 mol, 1 eq) is stirred in a mixture of acetonitrile/dioxane. HCl gas is bubbled through the reaction mixture. When all the starting material is consumed, the reaction mixture is basified with $NH_4OH$ and extracted with ethyl acetate. The organic layers are combined and are washed three times with water and brine. The organic phase is dried ($MgSO_4$) and concentrated in vacuo. Purification via flash chromatography gives the desired product 1-2.

Compound 1-3

Compound 1-2 is heated at 90° C. in a mixture of $POCl_3$/acetonitrile (90 mL/100 mL) for 5 hours. After cooling to room temperature, the reaction mixture is poured onto ice and is neutralized with a 6N NaOH solution. The product is purified by liquid chromatography. The chloro compound is dissolved in 800 mL of a mixture of water/methanol (1/1) cooled in an ice-bath. A bromine solution (12 mL of bromine in 100 mL $H_2O$/MeOH 1/1) is added dropwise to the cooled mixture. After 10 minutes, the solution is clearer and the LC/MS shows no chloro compound. The reaction mixture is concentrated, extracted with ethyl acetate (3×10 mL). The organic phases are combined, washed with water (2×50 mL), a brine solution (1×50 mL) and dried with sodium thiosulfate. The product is purified by liquid chromatography (ethyl acetate/hexane 1/1 Rf 0.7) to give 1-3.

Example 2

Synthesis of Intermediate for Structure (III)

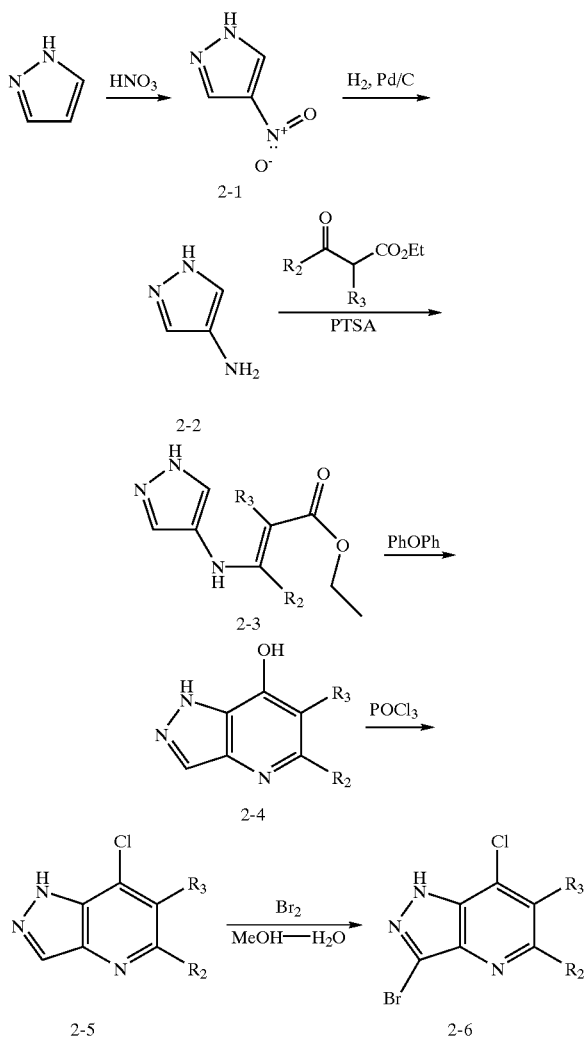

Compound 2-1

To a 5 L, 3-neck round-bottom flask equipped with a mechanical stirrer was charged 1500 mL of concentrated sulfuric acid and the solution cooled with an icebath. To this was charged 200 g (2940 mmol) of pyrazole keeping the reaction temperature <40° C. To the mixture was slowly added 200 mL (3200 mmol, 1.1 eq.) of 70% nitric acid keeping the reaction temperature between 50–60° C. The mixture was warmed to 55° C. and stirred for 3 hr. The mixture was cooled and poured over 3000 g of ice. The mixture was neutralized with 9300 mL of 6N sodium hydroxide. The precipitate was filtered and the filtrate extracted 3× with ethyl acetate. The combined organic phases were washed with brine and dried over magnesium sulfate. The solvent was removed in vacuo and the solid recrystallized from ethanol affording 111 g of 2-1 (33% yield). M.W. 113.08; TLC 1:1 ethyl acetate/hexane $R_f$=0.6; $GCt_R$=4.69 min.; MS $[M+1]^+$ 114; $^1H$ NMR ($CDCl_3$) (Pyrazole $GC_{TR}$=3.1–3.5 min).

Compound 2-2

To a 500-mL, Parr bottle under nitrogen atmosphere was charged 23.6 g (210 mmol) of 4-nitropyrazole 2-1, 100 mL of ethanol and 2.1 g of 10% palladium on Carbon. The mixture was shaken under a hydrogen atmosphere at 40 psi at ambient temperature for 3 hr. The mixture was flushed with nitrogen, filtered over a pad of celite, and the filter cake washed with ethanol. The solvent was removed in vacuo affording 16.6 g (95% yield) of 2-2 as a burgundy oil. M.W. 83.09; TLC 1:1 ethyl acetate/hexane $R_f$=0.1; $GCt_R$=3.66 min.; MS $[M+1]^+$ 84; $^1H$ NMR ($CDCl_3$).

Compound 2-3

To a 2 L round bottom flask equipped with a Dean-Stark trap and condenser was charged 150 g (1800 mmol) of 4-amino pyrazole 2-2, 800 mL of toluene, 200 mL (1620 mmol, 0.90 eq.) of ethylacetoacetate ($R_2C(O)CHR_3CO_2Et$ where $R_2$ is methyl and $R_3$ is H) and 16 g (84 mmol, 0.05 eq.) of p-toluene sulfonic acid monohydrate. The mixture was refluxed until TLC indicated only a residual amount of starting material. The solvent was removed in vacuo and the purple solid dissolved in ethyl acetate (approximately 2 L required). The crude solution was filtered through a plug of silica gel and the silica gel washed with ethyl acetate until no further product eluted. The solvent was removed in vacuo affording 2-3 as an off-white solid. M.W. 195.22; TLC 1:1 ethyl acetate/hexane Rf=0.3; MS $[M+1]'$ 196; $^1H$ NMR ($CDCl_3$).

Compound 2-4

To a 250 mL, round bottom flask was charged 70 mL of diphenyl ether and 30 mL of dioxane. The mixture was heated using an oil bath at 200° C. To the hot solution was carefully charged 30 g (153 mmol) of enamine 2-3. After approximately 10 minutes a solid began to precipitate and heating was continued for an additional 10–15 minutes. During this time the precipitate began to turn light brown and the heating was discontinued. The mixture was cooled to ambient temperature and diluted with ether. The solid was collected by filtration and washed with ether affording 2-4 as a light tan solid. The reaction was repeated with additional enamine 2-3 until all enamine prepared in the previous step was consumed. This afforded 122 g (46% yield) of 2-4. M.W. 149.15; MS $[M+1]^+$ 150; $^1H$ NMR ($CDCl_3$).

Compound 2-5

To a 500 mL, round bottom flask was charged 40 g (268 mmol) of quinoline 2-4, 125 mL of acetonitrile and 125 mL (1340 mmol, 5 eq.) of phosphorus oxychloride. The mixture was heated at 110° C. for 30 minutes. The mixture was cooled to ambient temperature and poured onto ice and carefully neutralized to pH 5 with 6N sodium hydroxide. The mixture was filtered and the filtrate extracted 3× with ethyl acetate. The combined organic phases were washed with brine and dried over magnesium sulfate. The solvent was removed in vacuo and the solid obtained combined with the initial precipitate. The precipitate was washed with 1:1 hexane/ether and dried in vacuo affording 41 g (91% yield) of 2-5 as a light tan solid. M.W. i67.6; TLC 1:1 ethyl acetate/hexane Rf=0.1; MS $[M+1]^+$ 168; $^1HNMR(CDCl_3)$.

Compound 2-6

To a 1 L, round bottom flask was charged 41 g (247 mmol)of 2-5 and 500 mL of 50% aqueous methanol. The solution was cooled in an ice-bath and 15 mL (296 mmol, 1.2 eq.) of bromine in 30 mL of 50% aqueous methanol was added dropwise gradually affording a precipitate. Upon completion of the addition, the mixture was stirred for 30 minutes. The slurry was filtered and the filter cake slurried with water and carefully neutralized with saturated sodium bicarbonate. The precipitate was filtered, washed with water and dried in vacuo affording 60 g (98% yield) of 2-6 as a light yellow powder. M.W. 246.5; TLC 1:1 ethyl acetate/hexane Rf=0.1; MS [M+1]+ 246, 248; $^1$H NMR (CDCl$_3$).

Example 3

Synthesis of Intermediate for Structure (IV)

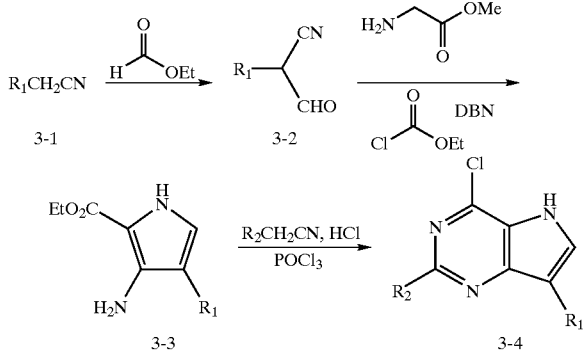

Compound 3-2

Under nitrogen atmosphere, ethyl formate (7.38 g, 99.6 mmol) in anhydrous THF (100 mL) is added dropwise to a stirred mixture of NaH (1.75 g, 72.9 mmol) and Compound 3-1 (37.5 mmol) in THF (100 mL). The mixture is stirred over night. Additional portions of NaH and HCO$_2$Et (2 equiv each) are added, and the mixture is refluxed for 30 min and then stirred at room temperature overnight. After solvent evaporation, the residue in ice cold water (100 mL) is adjusted to pH 6 with cold 6 N HCl and is extracted with CHCl$_3$ (3×100 mL). The extract is washed with water (100 mL), dried (Na$_2$SO$_4$), and evaporated. The residue is triturated with hexane, which is decanted. Column chromatography of the residue on silica gel (using CHCl$_3$ as eluant) gives compound 3-2.

Compound 3-3

A solution of compound 3-2 (5.31 mmol), methyl glycinate hydrochloride (1.00 g, 7.97 mmol), and sodium acetate (0.654 g, 7.97 mmol) in MeOH (40 mL) and H$_2$O (10 mL) is stirred at room temperature for 48 hr. The mixture is extracted with CHCl$_3$ (2×25 mL), and the organic extract is washed with water (20 mL), dried (Na$_2$SO$_4$), and evaporated. The residue (4.5 mmol) in dry CH$_2$Cl$_2$ (25 mL) is cooled to 0° C. and treated with 1,5-diazabicyclo(4.3.0)non-5-ene (DBN, 1.12 g, 9.04 mmol) followed by ethyl chloroformate (0.735 g, 6.78 mmol). After refrigeration for 24 h, 0.2 mL of DBN and 0.1 mL of ClCO$_2$Et are added to consume the small quantity of remaining starting material. An additional equivalent of DBN (0.6 g) is added, and the mixture is refrigerated for 20 h. Solvent is evaporated and the gummy residue is chromatographed on a silica gel column (CHCl$_3$ eluant) to give compound 3-3.

Compound 3-4

HCl gas is bubbled into a solution of compound 3-3 and acetonitrile in dioxane at room temperature. The reaction is monitored by TLC until all starting material is consumed. 10% aqueous ammonium hydroxide is added until the mixture is basic, followed by extraction with ethyl acetate. The organic layer is washed with water, dried over MgSO$_4$ and then evaporated to give a brown solid. The solid is dissolved in POCl$_3$ and is heated at 100° C. for 2 hrs. The excess POCl$_3$ is evaporated in vacuo and the residue is neutralized with 2N NaOH. Extraction with ethyl acetate followed by drying over MgSO$_4$ and evaporation gives a residue which is purified by flash chromatography on silica gel (Hexane/EtOAc, 4:1) to give compound 3-4.

Example 4

Synthesis of Intermediate for Structure (V)

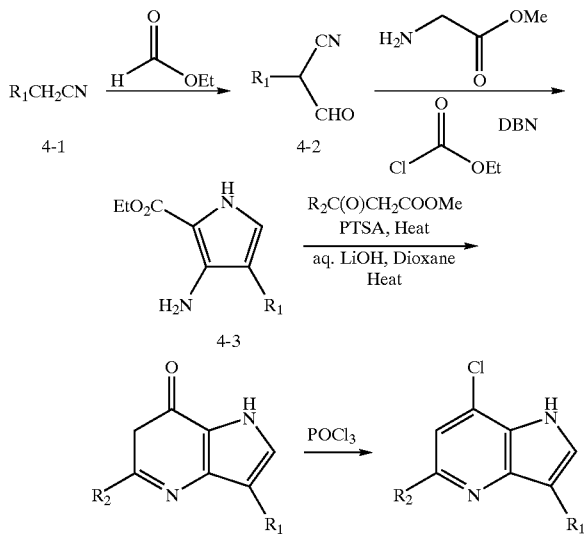

Compound 4-2

Under nitrogen atmosphere, ethyl formate (7.38 g, 99.6 mmol) in anhydrous THF (100 mL) is added dropwise to a stirred mixture of NaH (1.75 g, 72.9 mmol) and Compound 4-1 (37.5 mmol) in THF (100 mL). The mixture is stirred over night. Additional portions of NaH and HCO$_2$Et (2 equiv each) are added, and the mixture is refluxed for 30 min and then stirred at room temperature overnight. After solvent evaporation, the residue in ice cold water (100 mL) is adjusted to pH 6 with cold 6 N HCl and is extracted with CHCl$_3$ (3×100 mL). The extract is washed with water (100 mL), dried (Na$_2$SO$_4$), and evaporated. The residue is triturated with hexane, which is decanted. Column chromatography of the residue on silica gel (using CHCl$_3$ as eluant) gives compound 4-2.

Compound 4-3

A solution of compound 4-2 (5.31 mmol), methyl glycinate hydrochloride (1.00 g, 7.97 mmol), and sodium acetate (0.654 g, 7.97 mmol) in MeOH (40 mL) and H$_2$O (10 mL) is stirred at room temperature for 48 hr. The mixture is extracted with CHCl$_3$ (2×25 mL), and the organic extract is washed with water (20 mL), dried (Na$_2$SO$_4$), and evaporated. The residue (4.5 mmol) in dry CH$_2$Cl$_2$ (25 mL) is cooled to 0° C. and treated with 1,5-diazabicyclo(4.3.0)non-5-ene (DBN, 1.12 g, 9.04 mmol) followed by ethyl chloroformate (0.735 g, 6.78 mmol). After refrigeration for 24 h, 0.2 mL of DBN and 0.1 mL of ClCO$_2$Et are added to consume the small quantity of remaining starting material.

An additional equivalent of DBN (0.6 g) is added, and the mixture is refrigerated for 20 h. Solvent is evaporated and the gummy residue is chromatographed on a silica gel column (CHCl$_3$ as eluant) to give compound 4-3.

Compound 4-4

A solution of compound 4-3 (9.9 mmol), ethyl acetoacetate (9.9 mmol) and p-toluenesulfonic acid monohydrate (0.01 mmol) in 10 mL of xylene is refluxed for 2 hrs. Half of solvent is removed by slow distillation over 1 hour. The solution is allowed to cool to room temperature and a solution of potassium t-butoxide (9.8 mmol) in 24 mL of ethanol is added. This mixture is heated to 80° C. for 2 hrs. The mixture is diluted with ethyl acetate and washed with saturated NaCl solution. The organic layer is dried with sodium sulfate and concentrated in vacuo. The residue is triturated with ether. The solid obtained is treated with an aqueous solution of LiOH (18 mL, 1M) in methanol and the mixture is heated at reflux for 18 hr. The solution is poured into a solution of 1M HCl (18 mL). The solution is extracted with ethyl acetate, washed with brine, dried with sodium sulfate and concentrated in vacuo to give a solid which is heated in diphenyl ether at 230° C. for 1.5 hr. The solid 4-4 obtained after diluting with ether is dried in vacuo.

Compound 4-5

The solid 4-4 is heated at 100° C. in POCl$_3$ for 2 hrs then is allowed to cool to room temperature. The reaction mixture is poured into ice and neutralized with NaHCO$_3$. The solution is extracted with ethyl acetate. The organic layer is washed with brine, dried with sodium sulfate and concentrated in vacuo. Compound 4-5 is purified by flash chromatography on silica gel eluting with ethyl acetate-hexane (1:3).

Example 5

Alternative Synthesis of Intermediate for Structure (V)

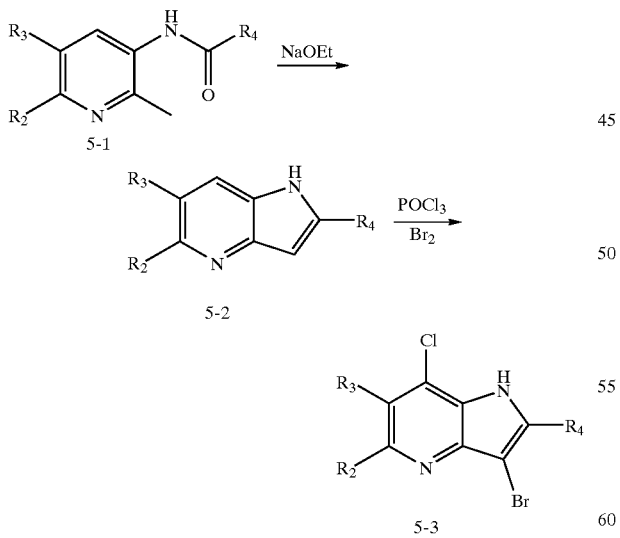

Compound 5-1

Substituted 3-aminopyridine (1 eq) is dissolved in pyridine and 1.5 eq of acetic anhydride is added. The mixture is stirred at room temperature for 1 day. Solvents are evaporated, water is added and the product is extracted with ethyl acetate. The organic layers are combined, washed with water and brine, dried with MgSO$_4$ and concentrated. The residue is purified by liquid chromatography to give 5-1.

Compound 5-2

A solution of sodium (1.7 g) and compound 5-1 (5 g) in anhydrous ethanol is evaporated to dryness and the residue is heated under dry hydrogen at 200° C. The temperature is slowly raised to 320° C. and maintained there for 15 minutes during which time the mixture darkens and a vigorous evolution of gas occurs. To the cooled mixture, water (100 mL) is added and the insoluble pale yellow residue filtered off, dried and sublimed at 150° C./0.5 mm to give 5-2.

Compound 5-3

The solid 5-2 is heated at 100° C. in POCl$_3$ for 2 hrs then is allowed to cool to room temperature. The reaction mixture is poured into ice and neutralized with NaHCO$_3$. The solution is extracted with ethyl acetate. The organic layer is washed with brine, dried with sodium sulfate and concentrated in vacuo. The residue is purified by flash chromatography on silica gel eluting with ethyl acetate-hexane (1:3). Like fractions are collected and the solvent is evaporated giving a residue which is dissolved in acetic acid. Bromine (2.2 g) in acetic acid is added dropwise and the mixture set aside. The needles which separated are crystallized from glacial acetic acid and are dissolved in water. The addition of 1 equivalent of N-sodium hydroxide gives compound 5-3.

Example 6

General Synthesis of Compounds of Structure (I)

The intermediates synthesized in Examples 1 through 5 may be used to make compounds of structure (I) according to the following general procedure:

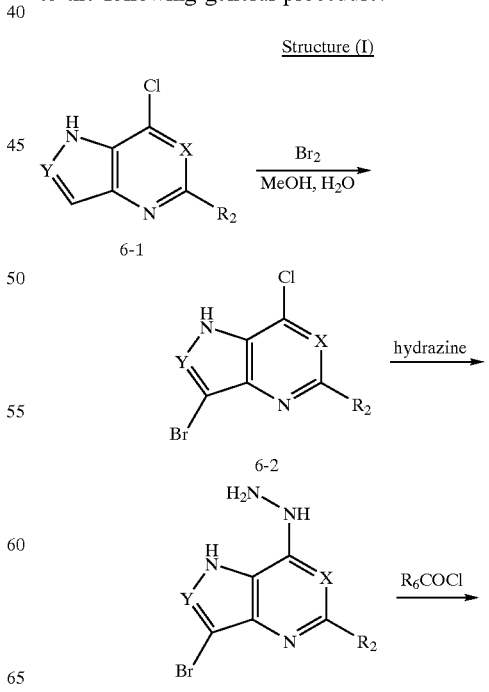

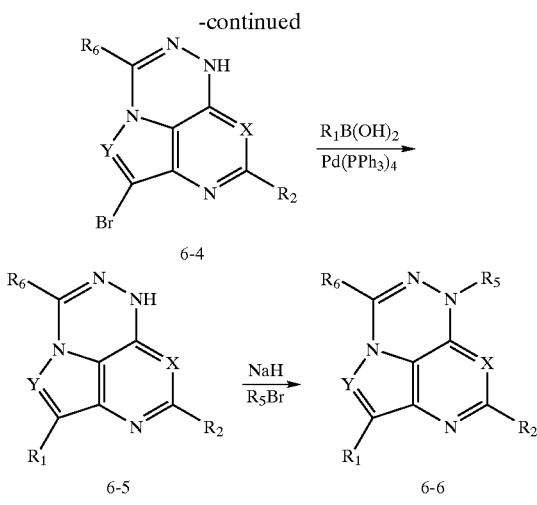

Compound 6-2

Chloro heterocycle 6-1 (40 mmol) from Example 1 through 5 is dissolved in 80 mL of a mixture of water/methanol (1/1) and is cooled in an ice-bath. A bromine solution (1.2 mL of bromine in 10 mL $H_2O$/MeOH 1/1) is added dropwise to the cooled mixture. After 10 minutes, the solution is clearer and the LC/MS shows no chloro compound. The reaction mixture is concentrated, extracted with ethyl acetate (3×100 mL). The organic phases are combined, washed with water (2×50 mL), a brine solution (1×50 mL) and dried with sodium thiosulfate. The product is purified by liquid chromatography (ethyl acetate/hexane 1/1 Rf 0.7) to give 6-2.

Compound 6-3

To compound 6-2 (10 mmol) in 20 mL of ethanol is added 3 mL of hydrazine and 300 mg of p-toluensulfonic acid. The mixture is refluxed overnight. Ethanol is evaporated and water added. The precipitate formed is filtered and concentrated in vacuo to give solid 6-3 (80% yield).

Compound 6-4

To compound 6-3 (0.012 mol) in 40 mL of dichloromethane at 0° C. is added $Et_3N$ (1.81 mL, 0.013 mol) followed by $R_6C(O)Cl$ (0.013 mol). The mixture is stirred at room temperature overnight. Saturated solution of bicarbonate is added, and the organic layer is separated. The water layer is extracted several times with ethyl acetate. Organic layers are combined, dried with $MgSO_4$, and concentrated in vacuo to give a tan solid. $POCl_3$ (50 mL) is added to the solid obtained and the mixture is refluxed for 24 hrs. Excess $POCl_3$ is evaporated in vacuo. Ice is added to the residue and the mixture stirred for 1 hr then neutralized with $Na_2CO_3$. The product is extracted with ethyl acetate, dried with $MgSO_4$ and concentrated in vacuo to give 6-4.

Compound 6-5

To bromo compound 6-4 (24 mmol) in 120 mL of toluene is added 43.2 mL of ethanol. To the mixture is added $R_1B(OH)_2$ (36 mmol, 1.5 eq.), followed by 39.6 mL of 2.0 M aqueous sodium carbonate solution, 24 mL of saturated barium hydroxide and 1.9 g (0.3 mmol) of tetrakis triphenylphosphine palladium. The mixture is heated at 90° C. for 16 hr. The mixture is cooled and the organic phase separated. The aqueous phase is extracted 3× with ethyl acetate and the combined organic extracts dried over magnesium sulfate and the solvent removed in vacuo. The crude product is purified by flash silica gel chromatography eluting with 9:1 dichloromethane/methanol affording compound 6-5 (69% yield).

Compound 6-6

To compound 6-5 (0.3 mmol) in DMF (10 mL) is added, under nitrogen atmosphere, NaH (9 mg, 0.36 mmol, 95%) and the mixture is stirred at room temperature for 15 min then $R_5$-halide (0.36 mmol) is added and the mixture stirred at room temperature overnight. DMF is removed in vacuo and the residue is dissolved in ethyl acetate and neutralized with 4 M HCl. The organic layer is dried with $MgSO_4$ and concentrated in vacuo. The residue obtained is purified by preparative TLC eluting with ethyl acetate-hexane (1:1) to give product 6-6 (i.e., compound of Structure (I)).

Example 7

Synthesis of Representative Compounds of Structure (I)

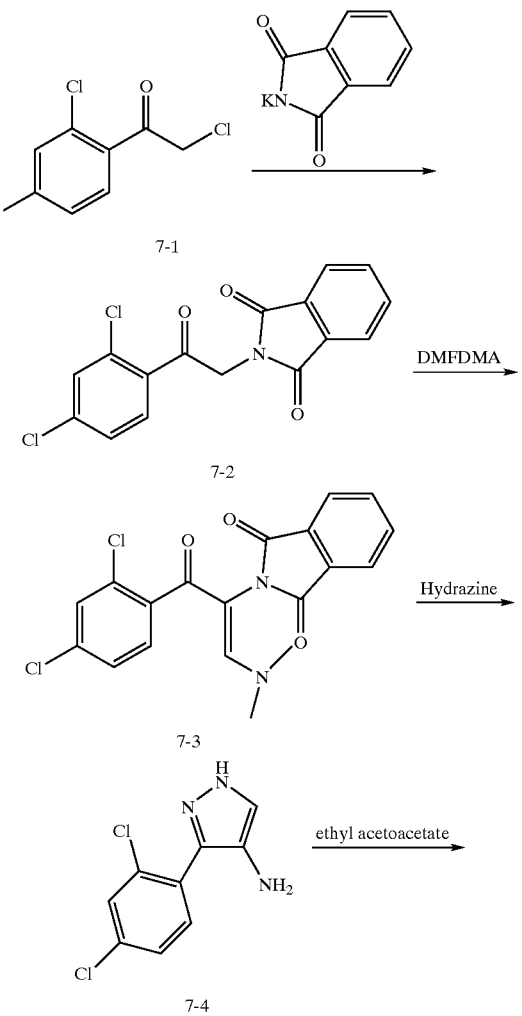

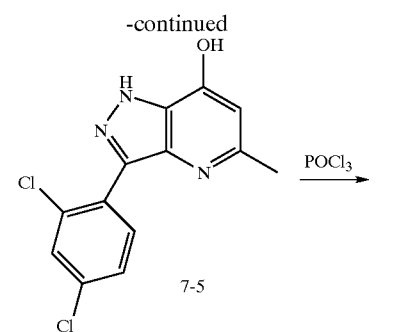

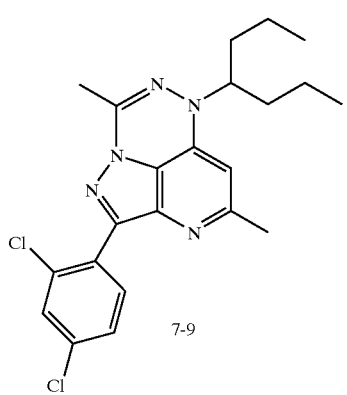

Compound 7-2

In a 5 L 3-neck flask equipped with a condenser and mechanical stirrer under a nitrogen atmosphere was charged 600 g (3239 mmol, 1.5 eq.) of potassium phthalimide followed by 1000 mL of anhydrous DMF. The stirring was started and 480 g (2148 mmol) of 2,2',4'-trichloroacetophenone 7-1 in 600 mL of anhydrous DMF was charged drop-wise over 20 minutes. The reaction mixture became warm upon addition. The mixture was stirred for 16 hours. The reaction was triturated with 400 mL of ether and filtered over a pad of celite. The filtrate was poured into 3 L of water, which became warm and was cooled with ice. The yellow precipitate was collected by filtration and washed with water. The solid was air dried and then charged to a 5 L 3-neck flask equipped with a mechanical stirrer and a Dean-Stark trap. The slurry was heated to reflux until no additional water was collected. The slurry was filtered and washed with cold toluene. The light yellow solid was dried in vacuo at 40° C. overnight affording 325 g (46% yield) of 7-2. M.W. 334.16; TLC 1:5 ethyl acetate/hexane, $R_f$=0.3; GC $t_R$=8.25 min.; MS [M+1]$^+$ 334.

Compound 7-3

In a 2 L 3-neck flask equipped with a distillation head and mechanical stirrer under a nitrogen atmosphere was charged 220 g (650 mmol) of 7-2 and 500 mL (3760 mmol, 5.6 eq.) of dimethylformamide dimethyl acetal. The mixture was heated to reflux and the methanol collected by distillation. After 2 hours, most of the residual DMFDMA was removed in vacuo affording a precipitate. The mixture was further triturated with ether. The solid was collected by filtration and washed with ether. The product was dried in vacuo at 40° C. overnight affording 205 g (81% yield) of 7-3. M.W. 389.24. TLC=1:1 Ethyl acetate/hexane, $R_f$=0.25; GC $t_R$=4.77 min.; MS [M+1]$^+$ 389.

Compound 7-4

In a 5L 3-neck flask equipped with a condenser and mechanical stirrer under a nitrogen atmosphere was charged 2000 mL of ethanol, 200 mL of water, and 195 g (500 mmol) of 7-3. Stirring was started and 113 g (1000 mmol, 2.0 eq.) of hydrazine monohydrobromide added portion-wise over 5 minutes. The slurry was heated to reflux for 5 hours. The reaction mixture was cooled and 6.9 g (216 mmol, 1.0 eq.) of anhydrous hydrazine was added. The reaction mixture was heated to reflux for 2 hours. The mixture was cooled and filtered over celite and the precipitate was washed with ethyl acetate. The filtrate was concentrated in vacuo affording 98 g (86% yield) of 7-4 as a brown foam. M.W. 228.08. TLC 1:1 ethyl acetate/hexane, $R_f$=0.2; GC $t_R$=6.79 min.; MS [M+1]$^+$ 228.

Compound 7-5

In a 2 L round-bottom flask equipped with a condenser, Dean-Stark trap and stir bar was charged 117 g (516.0 mmol) of 7-4, 1200 mL of toluene, 63.8 g (490 mmol, 0.95 eq.) of ethyl acetoacetate. Approximately 980 mg (0.5 mmol, 0.01 eq) of p-toluenesulfonic acid was added and agitation was started. The mixture was refluxed for 6 hr removing approximately 7 mL, of water. The mixture was cooled and the toluene removed in vacuo affording 162 g (98% yield) of a yellow oil. 70 g of the yellow oil was dissolved in 150 mL of diphenyl ether and the solution was poured into diphenyl ether (150 mL) preheated to 250° C. The reaction mixture was heated at 250° C. for 30 minutes. The heat was removed and the mixture was allowed to cool to 25° C. The mixture was then chilled with an ice bath and poured into 800 mL of a 10:1 hexane/ether mixture. The dark tan solid was filtered and washed with hexane. The solid was dried in vacuo at 40° C. affording 48.0 g of 7-5. M.W. 294.14.; MS [M+1]⁺ 294.

Compound 7-6

In a 250 mL round bottom flask equipped with a condenser and stir bar was charged 100 mL of anhydrous acetonitrile, 22 g (74.8 mmol) of 7-5 and 57.0 g (374 mmol, 5.0 eq.) of phosphorus oxychloride. The mixture was refluxed for 4 hr and the solvent was removed in vacuo. The dark oil was poured onto 400 g of crushed ice and neutralized with 4N potassium hydroxide solution. The precipitate was filtered and washed with water. The filtrate was extracted 3 times with ethyl acetate. The combined organic phases were washed with brine and dried over sodium sulfate. The extracted material was combined with the precipitate and dried in vacuo affording 16.1 g (69% yield) of tan solid 7-6. TLC 1:1 ethyl acetate/hexane Rf=0.6; M.W. 312.59; MS [M+1]⁺ 312.

Compound 7-7

To compound 7-6 (3 g) in 20 mL of ethanol was added 3 mL of hydrazine and 300 mg of p-toluensulfonic acid. The mixture was refluxed overnight. Ethanol was evaporated and water was added. The precipitate which formed was filtered and dried to give 2.5 g of solid 7-7. MS [M+1]⁺ 309.

Compound 7-8

To compound 7-7 (3 g, 0.012 mol) in 40 mL of dichloromethane was added at ice bath temperature Et₃N (1.81 mL, 0.013 mol) followed by acetyl chloride (0.96 mL, 0.013 mol). The mixture was stirred at room temperature overnight. Saturated solution of bicarbonate was added, and the organic layer was separated. The water layer was extracted several times with ethyl acetate. Organic layers were combined, dried with MgSO₄, and concentrated in vacuo to give a tan solid. POCl₃ (50 mL) was added to the solid obtained and the mixture was refluxed for 24 hrs. Excess POCl₃ was evaporated in vacuo. Ice was added to the residue and the mixture was stirred for 1 hr then neutralized with Na₂CO₃. The product was extracted with ethyl acetate, dried with MgSO₄ and concentrated in vacuo to give ~3 g of 7-8 which was used as is in the next step. MS [M+1]⁺ 332.

Compound 7-9

To compound 7-8 (100 mg, 0.3 mmol) in DMF (10 mL) was added, under nitrogen atmosphere, NaH (9 mg, 0.36 mmol, 95%) and the mixture was stirred at room temperature for 15 min then 4-bromoheptane (0.36 mmol) was added and the mixture was stirred at room temperature overnight. DMF was removed in vacuo and the residue was dissolved in ethyl acetate and neutralized with 4 M HCl to pH neutral. The organic layer was dried with MgSO₄ and concentrated in vacuo. The residue obtained was purified by preparative TLC eluting with ethyl acetate-hexane (1:1) to give 25 mg of 7-9. The material was further purified by preparatory HPLC. MS [M+1]⁺ 431.

Compound 7-10

Substitution of 4-bromoheptane with 3-bromopentane afforded the 3-pentyl alkylated product (7-10) which was purified by preparatory HPLC. MS [M+1]⁺ 406.

EXAMPLE 8

Alternative Synthesis of Representative Compound of Structure (I)

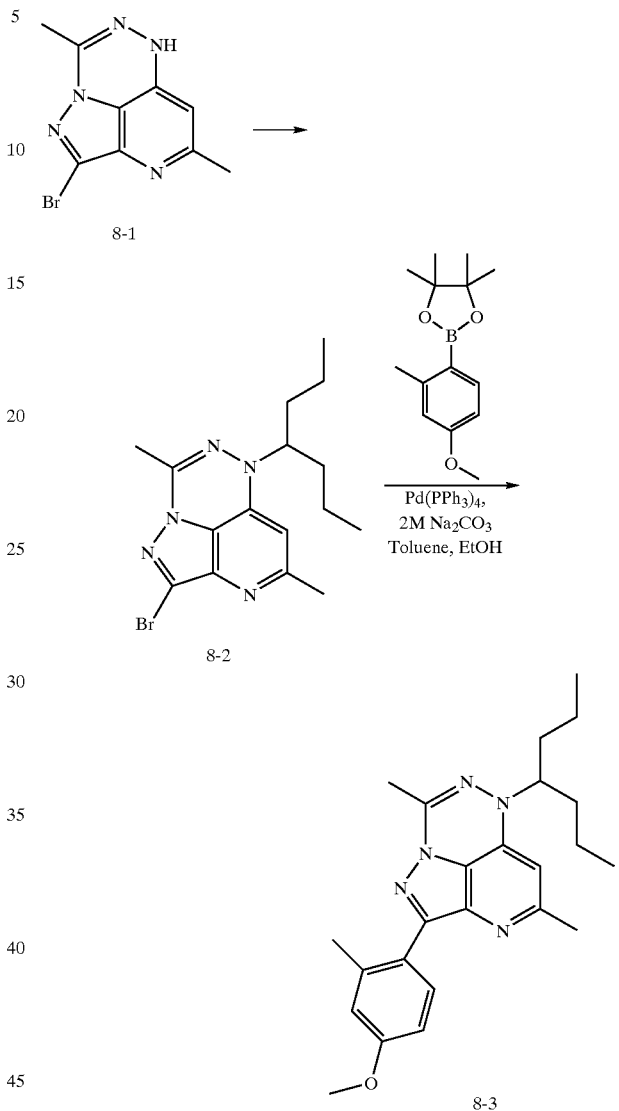

In an alternative embodiment, rather than addition of the R₁ group during initial synthesis steps, the R₁ group may be added at the end of the synthesis according to the following representative procedure.

Compound 8-2

To compound 8-1 (500 mg, 1.8 mmol) in DMF (20 mL) was added, under nitrogen atmosphere, NaH (54 mg, 2.2 mmol, 95%) and the mixture was stirred at room temperature for 15 min then 4-bromoheptane (2.2 mmol) was added and the mixture was stirred at room temperature overnight. DMF was removed in vacuo and the residue was dissolved in ethyl acetate and neutralized with 4 M HCl to pH neutral. The organic layer was dried with MgSO₄ and concentrated in vacuo. The residue obtained was purified by preparative TLC eluting with ethyl acetate-hexane (1:1) to give 125 mg of 8.2.

Compound 8-3

To a mixture of 8-2 (100 mg, 8.16 mmol), 0.4 mL of 2M sodium carbonate, ethanol (0.6 mL) and toluene (2 mL) was added under nitrogen atmosphere Pd(Ph3)4 (5% mol). The mixture was heated at 90° C. over night. The mixture was concentrated in vacuo and ethyl acetate and water were added. The organic layer was separated, dried over $MgSO_4$ and concentrated in vacuo. The residue obtained was purified by preparative TLC eluting with ethyl acetate-hexane (1:1) to yield 16 mg of compound 8-3.

Example 9

Representative Compounds Having CRF Receptor Binding Activity

The compounds of this invention may be evaluated for binding activity to the CRF receptor by a standard radioligand binding assay as generally described by DeSouza et al. (*J. Neurosci.* 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay is performed in 1.5 ml Eppendorf tubes using approximately $1 \times 10^6$ cells per tube stably transfected with human CRF receptors. Each tube receives about 0.1 ml of assay buffer (e.g., Dulbecco's phosphate buffered saline, 10 mM magnesium chloride, 20 $\mu$M bacitracin) with or without unlabeled sauvagine, urotensin I or CRF (final concentration, 1 $\mu$M) to determine nonspecific binding, 0.1 ml of [$^{125}$I] tyrosine—ovine CRF (final concentration ~200 pM or approximately the $K_D$ as determined by Scatchard analysis) and 0.1 ml of a membrane suspension of cells containing the CRF receptor. The mixture is incubated for 2 hours at 22° C. followed by the separation of the bound and free radioligand by centrifugation. Following two washes of the pellets, the tubes are cut just above the pellet and monitored in a gamma counter for radioactivity at approximately 80% efficiency. All radioligand binding data may be analyzed using the non-linear least-square curve-fitting program LIGAND of Munson and Rodbard (*Anal. Biochem.* 107:220, 1990).

Example 10

CRF-Stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (*Synapse* 1:572, 1987), with modifications to adapt the assay to whole cell preparations.

More specifically, the standard assay mixture may contain the following in a final volume of 0.5 ml: 2 mM L-glutamine, 20 mM HEPES, and 1 mM IMBX in DMEM buffer. In stimulation studies, whole cells with the transfected CRF receptors are plated in 24-well plates and incubated for 1 h at 37° C. with various concentrations of CRF-related and unrelated peptides in order to establish the pharmacological rank-order profile of the particular receptor subtype. Following the incubation, the media is aspirated, the wells rinsed once gently with fresh media, and the media aspirated. To determine the amount of intracellular cAMP, 300 $\mu$l of a solution of 95% ethanol and 20 mM aqueous hydrochloric acid is added to each well and the resulting suspensions are incubated at –20° C. for 16 to 18 hours. The solution is removed into 1.5 ml Eppendorf tubes and the wells washed with an additional 200 $\mu$l of ethanol/aqueous hydrochloric acid and pooled with the first fraction. The samples are lyophilized and then resuspended with 500 $\mu$l sodium acetate buffer. The measurement of cAMP in the samples is performed using a single antibody kit from Biomedical Technologies Inc. (Stoughton, Mass.). For the functional assessment of the compounds, a single concentration of CRF or related peptides causing 80% stimulation of cAMP production is incubated along with various concentrations of competing compounds ($10^{-12}$ to $10^{-6}$ M).

It will be appreciated that, although specific embodiments of the invention have been described herein for purposes of illustration, various modifications may be made without departing from the spirit and scope of the invention. Accordingly, the invention is not limited except as by the appended claims.

What is claimed is:
1. A compound having the following structure:

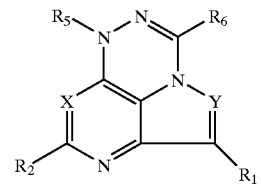

or a stereoisomer, prodrug or pharmaceutically acceptable salt thereof, wherein:
X is nitrogen or $CR_3$;
Y is nitrogen or $CR_4$;
$R_1$ is alkyl, substituted alkyl, —$NR_7R_8$, aryl, substituted aryl, heteroaryl or substituted heteroaryl;
$R_2$ is hydrogen, alkyl, alkoxy, thioalkyl or haloalkyl;
$R_3$ is hydrogen, alkyl, halo or haloalkyl;
$R_4$ is hydrogen, halogen, —$NR_7R_8$, alkyl, alkoxy, thioalkyl or haloalkyl;
$R_5$ is hydrogen, alkyl, substituted alkyl, aryl, substituted aryl, heteroaryl or substituted heteroaryl;
$R_6$ is hydrogen, alkyl, substituted alkyl, —$NR_7R_8$, —$OR_9$, —$SR_9$, aryl, substituted aryl, heteroaryl or substituted heteroaryl;
$R_7$ and $R_8$ are the same or different and independently hydrogen, alkyl, substituted alkyl, aryl, substituted aryl, heteroaryl or substituted heteroaryl; and
$R_9$ is alkyl, substituted alkyl, aryl, substituted aryl, heteroaryl or substituted heteroaryl.
2. The compound of claim 1 wherein X is $CR_3$.
3. The compound of claim 1 wherein X is nitrogen.
4. The compound of claim 1 wherein Y is $CR_4$.
5. The compound of claim 1 wherein Y is nitrogen.
6. The compound of claim 1 wherein $R_1$ is substituted aryl or substituted heteroaryl.
7. The compound of claim 1 wherein $R_5$ is alkyl, substituted alkyl, aryl or substituted aryl.
8. The compound of claim 6 wherein $R_5$ is alkyl, substituted alkyl, aryl or substituted aryl.
9. The compound of claim 7 wherein $R_1$ is —$NR_7R_8$.
10. The compound of claim 1 wherein both X and Y are nitrogen.
11. The compound of claim 1 wherein X is $CR_3$ and Y is nitrogen.
12. The compound of claim 1 wherein X is nitrogen and Y is $CR_4$.
13. The compound of claim 1 wherein X is $CR_3$ and Y is $CR_4$.

14. A composition comprising a compound of claim 1 in combination with a pharmaceutically acceptable carrier or diluent.

15. A method for treating stroke in a warm-blooded animal, comprising administering to the animal an effective amount of the pharmaceutical composition of claim 14.

16. A method for treating depression in a warm-blooded animal, comprising administering to the animal an effective amount of the pharmaceutical composition of claim 14.

17. A method for treating anxiety in a warm-blooded animal, comprising administering to the animal an effective amount of the pharmaceutical composition of claim 14.

18. A method for treating irritable bowel syndrome in a warm-blooded animal, comprising administering to the animal an effective amount of the pharmaceutical composition of claim 14.

\* \* \* \* \*